United States Patent
Baba et al.

(10) Patent No.: US 8,920,845 B2
(45) Date of Patent: Dec. 30, 2014

(54) METHOD OF PRODUCING MICROCAPSULES

(75) Inventors: Yoshinobu Baba, Nagoya (JP); Manabu Tokeshi, Nagoya (JP); Noritada Kaji, Nagoya (JP); Hideyoshi Harashima, Sapporo (JP); Kentaro Kogure, Sapporo (JP); Yasuo Shinohara, Tokushima (JP); Hiroshi Kuramoto, Tokushima (JP)

(73) Assignee: National University Corporation Nagoya University, Aichi (JP)

( * ) Notice: Subject to any disclaimer, the term of this patent is extended or adjusted under 35 U.S.C. 154(b) by 1266 days.

(21) Appl. No.: 12/513,237

(22) PCT Filed: Nov. 2, 2007

(86) PCT No.: PCT/JP2007/071388
§ 371 (c)(1),
(2), (4) Date: Jan. 25, 2010

(87) PCT Pub. No.: WO2008/053988
PCT Pub. Date: May 8, 2008

(65) Prior Publication Data
US 2010/0143482 A1 Jun. 10, 2010

(30) Foreign Application Priority Data
Nov. 2, 2006 (JP) .................. 2006-299450

(51) Int. Cl.
| | |
|---|---|
| *A61K 9/50* | (2006.01) |
| *A61K 9/51* | (2006.01) |
| *A61K 31/7088* | (2006.01) |
| *A61K 48/00* | (2006.01) |
| *A61K 9/127* | (2006.01) |
| *B01J 13/04* | (2006.01) |
| *C12N 15/87* | (2006.01) |

(52) U.S. Cl.
CPC ........... *A61K 48/0008* (2013.01); *A61K 9/1271* (2013.01); *A61K 9/1277* (2013.01); *A61K 9/5169* (2013.01); *A61K 9/5192* (2013.01); *A61K 48/0041* (2013.01); *B01J 13/04* (2013.01); *C12N 15/87* (2013.01)
USPC ........... 424/490; 424/450; 424/489; 514/44 R (58) Field of Classification Search
CPC ........... A61K 48/0008; A61K 48/0041; A61K 9/1271; A61K 9/1277; A61K 9/5169; A61K 9/5192; B01J 13/04; C12N 15/87
USPC ...................... 424/450, 490; 514/44
See application file for complete search history.

(56) References Cited

U.S. PATENT DOCUMENTS

| | | |
|---|---|---|
| 2002/0054912 A1 | 5/2002 | Kim et al. |
| 2004/0068019 A1 | 4/2004 | Higuchi et al. |

FOREIGN PATENT DOCUMENTS

| | | |
|---|---|---|
| JP | 2004-101493 | 4/2004 |
| JP | 2004-122107 | 4/2004 |
| JP | 2004-209430 | 7/2004 |
| JP | 2006-167521 | 6/2006 |
| WO | 02068104 | 9/2002 |
| WO | 2005-103106 | 11/2005 |
| WO | 2006-051153 | 5/2006 |

OTHER PUBLICATIONS

Kawakatsu et al. / Colloids and Surfaces A: Physicochem. Eng. Aspects 189 (2001) 257-264.*
International Search Report for PCT/JP2007/071388 dated Jan. 15, 2008.
Sawada, et al. Preparation of Melamine Resin Micro/Nanocapsules by using a Microreactor and Telomeric Surfactants, Macromolecular Materials Engineering, vol. 288, No. 12, p. 920-924, (2003).

* cited by examiner

*Primary Examiner* — Janet Epps-Smith
(74) *Attorney, Agent, or Firm* — Amin, Turocy & Watson, LLP (57) ABSTRACT

It is intended to provide a method whereby various kinds of microcapsules, which are usable in, for example, a gene vector, can be produced in a small amount. This production method comprises: feeding a fluid containing a substance to be encapsulated into at lease one (13) of material-feeding microchannels in a substrate in which these material-feeding microchannels (12, 13, 14) and a reaction microchannel (18) connected to these material-feeding microchannels are formed; feeding an envelop-forming fluid containing a material for forming envelopes into at least one of the other material-feeding microchannels (12, 14); and allowing the envelope-forming fluid and the fluid containing the encapsulated substance that converge in the reaction microchannel from each material-feeding microchannel to flow through the reaction microchannel while continuously maintaining the interface between the fluids formed at the confluence thereof.

10 Claims, 6 Drawing Sheets

METHOD OF PRODUCING MICROCAPSULES

TECHNICAL FIELD

The present invention relates to a method of producing microcapsules comprising a nanosize envelope and a substance encapsulated in that envelope. More specifically, the present invention relates to a method of producing microcapsules in microchannels formed on a substrate.

This international application claims priority based on Japanese Patent Application No. 2006-299450 filed on Nov. 2, 2006, and the entire content of that application is incorporated herein as a reference.

BACKGROUND ART

A large amount of research has been conducted concerning microcapsule structures, wherein various types of drugs are encapsulated in a so-called liposome composed of a lipid bilayer membrane, to be used as a material in drug delivery system (DDS). Recently, highly functional microcapsules have been developed that carry various substances (various ligands, etc.) on the surface thereof (for example, on the liposome surface).

Gene vectors (DNA vectors) for inserting a target gene (DNA, etc.) into a target cell play a major role in the field of gene therapy, for example. The development of artificial, non-virus-based gene vectors providing functionality that far surpasses that of traditional virus vectors has advanced, and more specifically, microcapsule vectors having properties that can be most suitably employed have been developed as artificial vectors.

As an example, patent document 1 describes a microcapsule (microdevice) called a multifunctional envelope-type nano device (MEND) that has been noted for its use as a gene vector. A MEND has a structure wherein a DNA core is surrounded by a lipid membrane, and expectations for its practical application are increasing because MENDs can increase the insertion rate into a target cell through modification of the lipid membrane surface with various functional molecules such as a target-binding ligand, cell membrane-penetrating peptide, and the like.

Patent document 1: Japanese Patent Application Laid-open No. 2006-167521.

DISCLOSURE OF THE INVENTION

However, previous methods of producing microcapsules such as MENDs, etc., have generally been very complex, and none has achieved high production efficiency. In the method described in patent document 1, for example, at least 30 hours are needed to produce a MEND with desired properties.

Moreover, although many types of microcapsules with different contents tailored to each test subject are required in usage modes such as gene vectors, with previous methods it has been impossible to carry out efficient, small-scale production that is provided for such individual needs. More specifically, with the method described in patent document 1 it is impossible over a short period of time to achieve efficient, small-scale production of many types of MENDs having a variety of core members (e.g., DNA) and/or ligands carried on the external surface thereof.

Thus, the present invention was meant for solving these conventional problems concerning the production of microcapsules such as MENDS, and the object thereof is to provide a method whereby a variety of microcapsules that can be used as gene vectors can be produced in small amounts. In addition, a further object of the present invention is to provide preferred materials for such a production method.

In accordance with the present invention, a method is provided for producing a microcapsule having a diameter of 1 μm or less and comprising an envelope and a substance encapsulated in that envelope.

The method of the present invention comprises: (1) preparing a substrate in which a plurality of material-feeding microchannels and a reaction microchannel connected to the plurality of material-feeding microchannels are formed; (2) feeding a fluid containing the above substance to be encapsulated (hereinafter, simply referred to as "encapsulated substance") into at least one of the plurality of material-feeding microchannels; (3) feeding an envelope-forming fluid containing an envelope-forming material into at least another one of the plurality of material-feeding microchannels; (4) forming a microcapsule such that the encapsulated substance is encapsulated within the envelope in the reaction microchannel by causing the envelope-forming fluid and the fluid containing the encapsulated substance that converge in the reaction microchannel from each material-feeding microchannel to flow through the reaction microchannel while continuously maintaining the interface between the fluids formed at the confluence thereof; and (5) collecting the fluid containing the microcapsule flowing through the reaction microchannel.

Herein the term "microcapsule" refers to a nanosize, microparticle structure having an envelope (shell) of the aforementioned size and an encapsulated substance contained therein as the main elements thereof. A typical microcapsule includes a so-called liposome. Herein, the term "fluid" includes various materials in a liquid state such as a solution, dispersion, and the like.

Furthermore, herein the term "microchannel" refers to a fine channel (typically a microsize channel with a width of 1000 μm or less) formed on a substrate by a variety of methods.

With the method having the above features, a desired microcapsule (e.g., a liposome) can be efficiently produced within a fluid fed into a microchannel (fine channel) formed on a substrate. In a suitably sized microchannel, the surface area per unit volume (flow rate) of the plurality of material fluids fed thereto can be markedly increased. As a result, the contact area between the material fluids, i.e., the interface area, increases, and high reaction efficiency at that interface can be realized. Moreover, because the reaction system itself is of an extremely small scale, the reaction conditions for synthesis (generation) of the microcapsules can be easily controlled, and savings in energy and resources can be realized.

Therefore, the method of the present invention enables the efficient production of a plurality of types of microcapsules with distinctive features (e.g., ones wherein the composition of the encapsulated substance, envelope surface-modifying substance, etc., differ) in a short time using little energy, and without discharging a large amount of waste or using a large-scale facility (in other words, a variety of microcapsules can be produced in small quantities).

Preferably, the width of the material-feeding microchannels and the reaction microchannel ranges from 10 μm to 500 μm. Microcapsule production featuring a more efficient interface reaction between the fluids (fluid-fluid interface reaction) can be realized by using fine microchannels of this size.

A preferred mode of the method of producing a microcapsule disclosed herein utilizes, as the substrate, a substrate in which three or more material-feeding microchannels are provided (typically, three are provided), and the three or more material-feeding microchannels are formed such that they are all connected to the reaction microchannel at a point. In addition, the preferred mode is also one feeding the envelope-forming fluid into any two or more of the three or more material-feeding microchannels such that the envelope-forming fluid flows on both sides of the fluid containing the encapsulated substance flowing through an area of one part of the reaction microchannel while maintaining an interface with the fluid containing the encapsulated substance.

Establishing a confluent state in the reaction microchannel with a type of substrate where these three or more material-feeding microchannels simultaneously connected to a single reaction microchannel (typically, a type of substrate with a trident-shaped intersection where three material-feeding microchannels are connected to a single reaction microchannel as in the mode exemplified below), insures a larger interface surface area between the envelope-forming fluid and the fluid containing the encapsulated substance, and as a result, microcapsules can be produced even more efficiently.

The method disclosed herein is particularly suitable for the small-volume production of various microcapsules wherein all or part of the encapsulated substance is a polynucleotide and the envelope is a membrane comprising a lipid. Therefore, the method of the present invention enables very efficient production on an extremely small scale of microcapsules suitable for use as a gene vector such as the MENDS described above.

A preferred mode of the method of producing a microcapsule that can serve as a gene vector uses a complex of a polynucleotide and a cationic compound as the encapsulated substance.

Generally, a polynucleotide such as DNA (gene to be inserted) normally carries a negative charge, and a condensed complex held together by electrostatic interactions can be formed by combining the polynucleotide with a cationic compound. This kind of condensation facilitates the insertion of the encapsulated substance (in this case, a polynucleotide) into the envelope. In addition, a complex can be given an overall positive or negative charge depending on the composition ratio of the cationic compound to the polynucleotide. In general, cell membranes are negatively charged, so a microcapsule (gene vector) enabling more efficient insertion of a gene into a cell can be produced by using such a positively charged complex as the encapsulated substance.

The method of a preferred mode when such a complex is used includes performing beforehand a step of producing the complex. More specifically, the step of producing the complex comprises: (1) preparing a substrate in which a plurality of material-feeding microchannels and a reaction microchannel connected to the plurality of material-feeding microchannels are formed; (2) feeding a fluid containing the polynucleotide into at least one of the plurality of material-feeding microchannels; (3) feeding a fluid containing the cationic compound into at least another of the plurality of material-feeding microchannels; (4) forming the complex in the reaction microchannel by causing the fluid containing the polynucleotide and the fluid containing the cationic compound that converge in the reaction microchannel from each material-feeding microchannel to flow through the reaction microchannel while continuously maintaining the interface between the fluids formed at the confluence thereof; and (5) collecting the fluid containing the complex that has flowed through the reaction microchannel.

By combining the process of producing the above complex, which is a starting material for production of such a microcapsule, as a preliminary step, the entire microcapsule production process can be carried out even more efficiently.

For the same reasons as described above, an encapsulated substance (i.e., the above complex) required for a microcapsule to be utilized as a gene vector can be produced efficiently with little energy, and without discharging a large amount of waste or using a large-scale facility.

Moreover, as the substrate for producing the complex of the polynucleotide and the cationic compound in the method of the above mode, using a substrate in which three or more material-feeding microchannels are provided and where the three or more material-feeding microchannels are formed such that they are all connected to the reaction microchannel at a single point is particularly preferred. In addition, a non-material-containing-fluid that contains neither a polynucleotide nor a cationic compound (typically, water or another aqueous medium that does not contain a polynucleotide or cationic compound) is fed into at least one of the material-feeding microchannels, and the fluid containing the polynucleotide is fed into at least one of the material-feeding microchannels and the fluid containing the cationic compound is fed into at least one other of the material-feeding microchannels such that the fluid containing the polynucleotide flows on one side of the non-material-containing fluid flowing through an area of one part of the reaction microchannel while maintaining an interface with the non-material-containing fluid, and such that the fluid containing the cationic compound flows on the other side of the non-material-containing fluid while maintaining an interface therewith.

By using a substrate with such a configuration (typically, a type of substrate with a trident-shaped intersection wherein three material-feeding microchannels are connected to a single reaction microchannel as in the mode exemplified below) and establishing the mode of interaction of the various flows (i.e., three types of fluids composed of the non-material-containing fluid, fluid containing a polynucleotide, and fluid containing a cationic compound) in the reaction microchannel as described above, it can be ensured that the interface area for forming the complex will be larger, and as a result, the complex can be produced even more efficiently.

In accordance with the present invention, a substrate is provided with microchannels that can suitably be used for carrying out the method of producing a microcapsule (or the method of producing an encapsulated substance in the preliminary step noted above) of the various modes disclosed herein.

Preferably, it is a substrate for producing a microcapsule having a diameter of 1 μm or less and comprising an envelope and a material encapsulated in that envelope, and includes three or more material-feeding microchannels and a reaction microchannel connected to the plurality of material-feeding microchannels. Furthermore, the three or more material-feeding microchannels are formed such that they are all connected to the reaction microchannel at a point. Preferably, the width of the material-feeding microchannels and the reaction microchannel ranges from 10 μm to 500 μm.

Furthermore, the form of the "substrate" is not particularly limited herein provided it can function as a microreactor for carrying out the method of producing a microcapsule (or method of producing an encapsulated substance in the preliminary step described above) of the present invention. Typically, it is a flat substrate (including plates on a small scale that can be designated a so-called microchip), but is not limited thereto, and for example, it can be in the form of fine tubes configured such that the interiors thereof constitute the above microchannels.

BEST MODE FOR CARRYING OUT THE INVENTION

The preferred exemplary mode of the present invention is described below. Matters other than those specifically stated herein (for example, preferred mode of microchannels, or features of the encapsulated substance and envelope, and production method thereof) that are necessary for carrying out the present invention (for example, method of producing a substrate providing microchannels, or means of feeding fluid into the microchannels) can be taken as matters of design for a person skilled in the art based on prior art in the field. The present invention can be carried out based on the content disclosed herein and common technical knowledge in this field.

The method disclosed herein is a method of producing microcapsules by a reaction at the interface between two different fluids fed into fine microchannels, and it is not particularly limited with respect to the shape and material of the substrate (microreactor) being used provided that the object of the present invention is realized. Typically, it can be a plate-shaped microchip (base material), but other shapes are also possible.

The material constituting the substrate is not particularly limited herein, and materials constituting microchips known from prior art are suitable. Preferred examples include a substrate material made of glass such as quartz glass, a substrate material made of silicon, or a substrate material made of a synthetic resin comprising polyethylene, polypropylene, polycarbonate, polystyrene, polymethyl methacrylate, polytetrafluoroethylene, polydimethylsiloxane, and the like.

Figure 1:
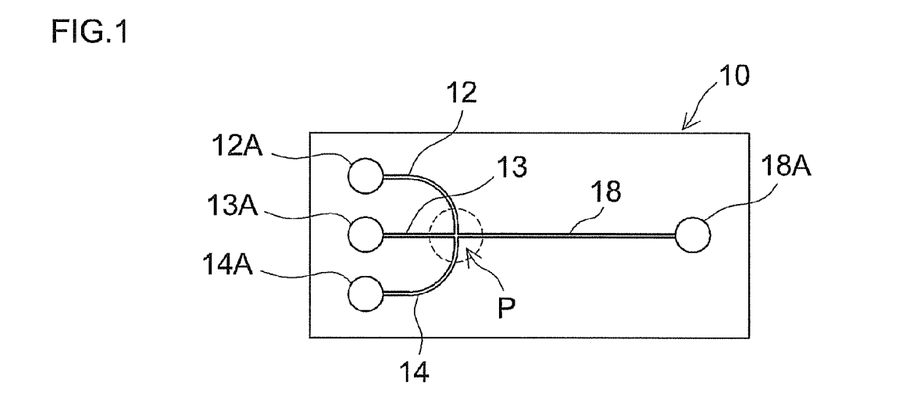
FIG. 1 is an enlarged plan view schematically illustrating the configuration of the substrate as in one exemplary mode of the present invention.

As a typical example, FIG. 1 schematically illustrates a microchip-shaped substrate material (microreactor) 10 suitable for carrying out the method of the present invention. A total of three material-feeding microchannels 12, 13, 14 and one reaction microchannel 18 are formed on the substrate (microchip) 10. As illustrated, the three material-feeding microchannels 12, 13, 14 are formed to connect with reaction microchannel 18 at a single point P. In addition, reservoirs (inlets) 12A, 13A, 14A in which material fluid (liquid) can be temporarily stored are formed on the upstream side of the material-feeding microchannels 12, 13, 14, and on the other side a reservoir (outlet) 18A in which the post-reaction fluid can be temporarily stored is formed on the downstream side of the reaction microchannel 18. The substrate 10 is more convenient as a microchip as a result.

Figure 2:
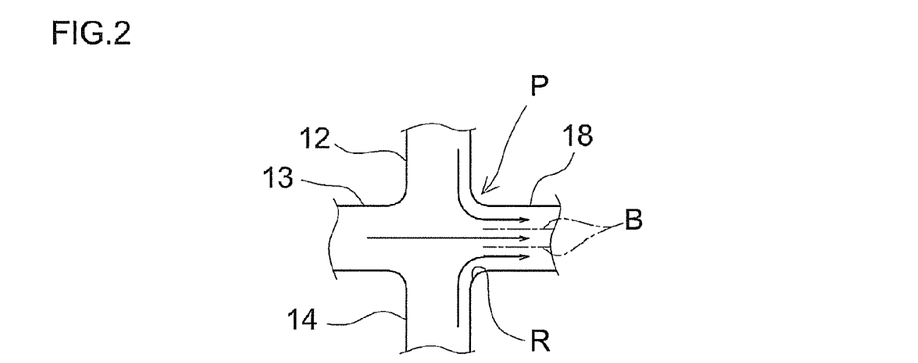
FIG. 2 is an enlarged plan view schematically illustrating the essential parts of the substrate shown in FIG. 1.

FIG. 2 shows an enlarged view of the junction point P of the microchannels. As shown in the drawing, the member at point P is formed such that each of the material-feeding microchannels 12, 13, 14 intersects orthogonally with its adjacent channels, and the material-feeding microchannels 12, 13, 14 and the reaction microchannel 18 intersect in the shape of a cross.

As shown by the arrows in FIG. 2, by forming such a connection, the fluid flowing through the central material-feeding microchannel 13 proceeds straight ahead and is fed into the reaction microchannel 18, and the fluids flowing through the material-feeding microchannels 12, 14 on both sides thereof are fed into the reaction microchannel 18 such that they sandwich the fluid fed from the central material-feeding microchannel 13 on both sides.

As shown by the dotted lines in FIG. 2, interfaces (fluid-fluid interfaces) B among the fluids flowing from the various material-feeding microchannels 12, 13, 14 are formed in the reaction microchannel 18.

In addition, as shown in FIG. 2, the corner member R of the microchannel side-walls that constitute the member at point P (particularly, the two side-wall corner members R that are adjacent to the reaction microchannel 18) is formed into a rounded surface (R surface). Therefore feeding of the fluid from the various material-feeding microchannels 12, 13, 14 into the reaction microchannel 18 can be carried out smoothly and the above interface B can be readily maintained. Although it is not illustrated herein, a similar effect can be achieved when the corner member R is formed like C surface instead of a rounded surface (R surface).

The shape of the microchannels (width, depth, etc.) is not particularly limited herein provided the reaction generating the target product (microcapsule or encapsulated substance such as the aforementioned complex) can be carried out at the above interface. However, a suitable microchannel width ranges from 1 μm to 1000 μm, and preferably 10 μm to 500 μm. With microchannels of such a size, typically microcapsules can be formed with a diameter of 10 to 1000 nm, and preferably about 10 to 500 nm (particularly about 50 to 200 nm). Moreover, the method of the present invention can provide microcapsules with an extremely narrow particle size distribution (i.e., particles of essentially the same size).

The widths of the material-feeding microchannels 12, 13, 14, and the reaction microchannel 18 are the same in the example shown in FIG. 2, but they can differ. For example, the width of the reaction microchannel 18 can be made greater than the widths of the material-feeding microchannels 12, 13, 14.

Furthermore, the depth of the microchannels is not particularly limited herein provided an interface can be maintained. A depth ranging from 1 μm to 500 μm is suitable, and a range of 5 μm to 300 μm is preferred. For example, microchannels with a width of about 50 to 200 μm and a depth of about 10 to 50 μm are preferred.

Methods used to manufacture conventional microchips (microreactors) can be employed to form a reaction microchannel and material-feeding microchannels with the aforementioned shape on a substrate material.

For example, methods for forming the aforementioned kinds of microchannels 12, 13, 14, 18 and reservoirs 12A, 13A, 14A, 18A on a glass substrate material include a method using conventional photoresist and etching. For example, a predetermined pattern and/or size of microchannels and reservoir wells can be formed on a substrate material by forming a silicon film on the substrate, coating the same with photoresist, forming a pattern thereon, and then etching with a suitable chemical. Additionally, an injection molding method can be applied when a resin substrate is used. The methods per se for forming microchannels on such a substrate (microchip, etc.) have been carried conventionally, and because they do not characterize the present invention, a more detailed explanation thereof is omitted herein.

Preferably, the walls of the microchannels are coated with a suitable coating material to prevent the material or the microcapsules produced within the microchannels from adhering to the walls of the microchannels. For example, it is possible to inhibit adhesion to the channel walls of a polynucleotide, protein, etc., by coating the inside walls of the channels with a polymer such as polyethylene glycol (PEG), a silicone resin, and the like.

Figure 3:
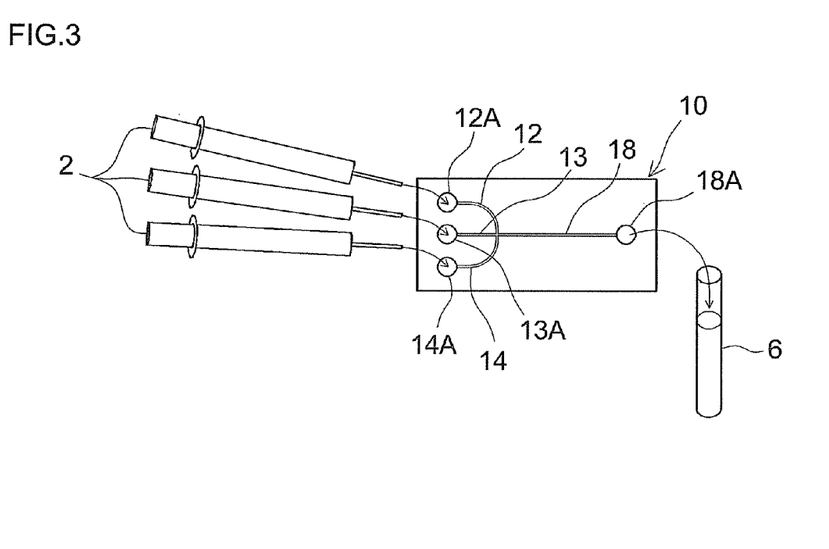
FIG. 3 is an explanatory drawing schematically illustrating one example of a microreactor configuration suitable for carrying out the method of the present invention.

As shown in FIG. 1, the substrate 10 can be suitably used as a microreactor (reaction vessel). FIG. 3 illustrates a simple structure of a microreactor.

As shown in the drawing, a feeding tube 2 equipped with a syringe pump is connected independently to each of the reservoirs (inlets) 12A, 13A, 14A of the material-feeding microchannels 12, 13, 14 formed on the substrate 10. Fluids (various liquid materials such as solutions, liquid dispersions, etc.) of different compositions can be provided to each of the material-feeding microchannels 12, 13, 14 at a suitable flow rate (for example, 0.05 to 100 μL/min, preferably 0.5 to 20 μL/min). Furthermore, by connecting a collection tube 6 to the reservoir (outlet) 18A of the reaction microchannel 18 formed on the substrate 10, it is possible to collect the post-reaction fluid (i.e., fluid containing microcapsules). FIG. 3 is an extremely simplified structure for the purpose of describing the present invention, and in a real microreactor many accessories that are not illustrated herein can be provided as needed. For example, control devices (typically, a computer (PC)), various monitoring devices, sensors, etc., can be provided to control the flow (flow rate) of the material fluid that is fed into each of the material feeding microchannels by controlling the operation of the aforementioned syringe pumps.

Microcapsules with desired properties can be produced efficiently by a reaction at a micro-interface by using a substrate providing the kind of material-feeding microchannels and reaction microchannel described above.

The fluid (i.e., liquid material) that forms the envelope of the microcapsules is typically one prepared by containing the material constituting the envelope in a suitable solvent. Various materials can be used as the material constituting the envelope, but an amphipathic substance capable of forming a stable membrane (envelope) in an organic solvent or aqueous solvent is especially preferred, and typically a lipid is used therefor. In other words, the envelope that is especially preferred for carrying out the present invention is a membrane comprising a type of lipid that constitutes a conventional liposome (particularly a membrane comprising a lipid bilayer). Typically the envelope of the aforementioned MEND is fainted by a lipid membrane comprising a lipid bilayer.

A phospholipid, glycolipid, sterol, saturated or unsaturated fatty acid, and the like can be noted as a preferred lipid constituting the envelope.

Examples of phospholipid include: phosphatidylcholines (for example, dioleoyl phosphatidylcholine, dilauroyl phosphatidylcholine, dimyristoyl phosphatidylcholine, dipalmitoyl phosphatidylcholine, and distearoyl phosphatidylcholine); phosphatidylglycerols (for example, dioleoyl phosphatidylglycerol, dilauroyl phosphatidylglycerol, dimyristoyl phosphatidylglycerol, dipalmitoyl phosphatidylglycerol, and distearoyl phosphatidylglycerol); phosphatidylethanolamines (for example, dioleoyl phosphatidylethanolamine, dilauroyl phosphatidylethanolamine, dimyristoyl phosphatidylethanolamine, dipalmitoyl phosphatidylethanolamine, and distearoyl phosphatidylethanolamine); phosphatidylserine; phosphatidylinositol; phosphatidic acid; cardiolipin; sphingomyelin, egg yolk lecithin; soy lecithin; and the hydrogenated forms thereof.

Examples of glycolipids include glyceroglycolipids (for example, sulfoxyribosylglyceride, diglycosyldiglyceride, digalactosyldiglyceride, galactosyldiglyceride, and glycosyldiglyceride); and sphingoglycolipids (for example, galactosylcerebroside, lactosylcerebroside and ganglioside).

Examples of sterols include sterols of animal origin (for example, cholesterol, cholesterol succinate, lanosterol, dihydrolanosterol, desmosterol, and dihydrocholesterol); sterols of plant origin (for example, stigmasterol, sitosterol, campesterol, and brassicasterol); and sterols of microbial origin (for example, zymosterol and ergosterol).

Examples of the saturated or unsaturated fatty acids include saturated or unsaturated fatty acids of 12 to 20 carbon atoms such as palmitic acid, oleic acid, stearic acid, arachidonic acid, myristic acid, etc.

More specifically, when producing microcapsules to be used as a gene vector such as the aforementioned MEND, the use of a lipid with high membrane fusion capability is preferred as the lipid to be used as the envelope-forming material. By using a lipid with high membrane fusion capability the release efficiency from an endosome can be increased when a gene vector (microcapsule) is taken up by a cell. Examples of lipids with high membrane fusion capability include dioleoyl phosphatidylethanolamine, cardiolipin, and cholesterol succinate.

Lipids are classified as neutral, cationic, and anionic. Examples of neutral lipids include diacyl phosphatidylcholine, diacyl phosphatidylethanolamine, cholesterol, ceramide, sphingomyelin, cephalin, and cerebroside. Examples of cationic lipids include DODAC (dioctadecyldimethylammonium chloride), DOTMA (N-(2,3-dioleyloxy) propyl-N,N,N-trimethylammonium), DDAB (didodecylammonium bromide), DOTAP (1,2-dioleoyloxy-3-trimethylammonio propane), DC-Chol (3β-N-(N',N'-dimethyl-aminoethane)-carbamol cholesterol, DMRTE (1,2-dimyristoyloxypropyl-3-dimethylhydroxyethyl ammonium), and DOSPA (2,3-dioleyloxy-N-[2-(spermine carboxamido) ethyl]-N,N-dimethyl-1-propanaminium trifluoroacetate). Examples of anionic lipids include cardiolipin, diacyl phosphatidylserine, diacyl phosphatic acid, N-succinyl phosphatidylethanolamine (N-succinyl PE), phosphatidic acid, phosphatidylinositol, phosphatidylglycerol, phosphatidyl ethylene glycol, and cholesterol succinate.

The charge of the envelope to be formed can be adjusted by paying attention to such charge differences and selecting the envelope-forming material (lipid material) thereby. For example, an envelope having an overall positive charge can be formed by using mainly a cationic lipid material. On the other hand, an envelope having an overall negative charge can be formed by using mainly an anionic lipid material.

Additionally, various components other than the lipid can be included in the envelope-forming fluid (liquid material).

For example, a sterol, glycerin, or fatty acid ester thereof (e.g., triolein, trioctanoin), etc., can be added thereto as a membrane stabilizer.

Additionally, tocopherol, propyl gallate, ascorbyl palmitate, butylated hydroxytoluene, and the like can be added as an antioxidant.

Furthermore, a charged substance other than the main lipid material can be suitably added to adjust the positive or negative charge of the envelope. Examples of charged substances imparting a positive charge include saturated or unsaturated aliphatic amines such as stearylamine and oleylamine; and saturated or unsaturated cationic synthetic lipids such as dioleoyl trimethylammonium propane and the like. Moreover, a suitable amount of a cationic surfactant can be added. Conversely, dicetyl phosphate, cholesteryl hemisuccinate, phosphatidylserine, phosphatidylinositol, phosphatidic acid, and the like can be added as a charged substance that imparts a negative charge. Additionally, a suitable amount of an anionic surfactant can be added.

Furthermore, various peptide and protein components can be added to maintain membrane structure and impart functionality to the liposome. Examples of these types of substances include a peripheral membrane protein (or peptide), and an integral membrane protein (or peptide).

On the other hand, various polymer compounds and complexes thereof can be noted as the encapsulated substance constituting the microcapsules. When used for gene therapy or another biochemical application, suitable examples of the encapsulated substance include biological materials or reagents such as DNA, RNA, or another polynucleotide, and an oligopeptide, polypeptide, protein, saccharide, and the like. Preferred examples are complexes of DNA and various organic polymers (e.g., a polypeptide).

For example, by establishing opposing positive and negative charges for the envelope and encapsulated substance the efficiency of uptake of the encapsulated substance by the envelope can be increased by the electrostatic interactions thereof. More specifically, with an envelope formed from an amphipathic phospholipid, etc., in an aqueous solvent (lipid bilayer membrane), the surface of the membrane is negatively charged in general. Therefore, in such a case a positively charged encapsulated substance is more easily taken up by the negatively charged envelope.

A means for imparting a positive charge to a negatively charged polynucleotide such as DNA includes, for example, forming a complex with a cationic compound (cationic polymer). Examples of a cationic compound include a cationic lipid (e.g., Lipofectamine™ (Invitrogen)); a homopolymer or copolymer of a basic amino acid such as polylysine, polyarginine, lysine/arginine copolymer, etc., or a derivative thereof (e.g., a stearylated derivative); and a polycationic polymer such as polyethylene imine, poly(allylamine), poly(diallyl dimethyl ammonium chloride) and glucosamine, protamine sulfate, and the like.

Forming a complex with a long-chain cationic polymer such as polylysine (poly-L-lysine) is preferred. Furthermore, such a complex enables condensation with a long-chain substance such as DNA or another polynucleotide, and as a result, the envelope uptake efficiency can be increased by both the physical and electrochemical aspects.

Furthermore, by adjusting the composition ratio of the cationic compound, the charge of the complex as a whole can be adjusted (in other words, whether it is charged slightly positive or slightly negative overall).

Conversely, if the encapsulated substance is a cationic compound (e.g., a basic protein), a complex can be formed with an anionic compound (e.g., a polynucleotide consisting of a random sequence that does not function as a gene). As described above, in this case the charge of the complex as a whole can be adjusted (in other words, whether it is charged slightly positive or slightly negative overall) by adjusting the ratio of the anionic compound in the composition. Examples of anionic compounds include an anionic lipid; homopolymer or copolymer of an acidic amino acid such as polyaspartic acid, etc., or a derivative thereof; and a polyanionic polymer such as xanthan gum, a carboxyvinyl polymer, carboxymethyl cellulose/polystyrene sulfonate, a polysaccharide, and carrageenan.

In accordance with the method described herein, the step of producing the above complex as a preliminary step in the process of producing the microcapsules can be carried out by using the kind of substrate 10 illustrated in FIG. 1. For example, a fluid (liquid material) containing the target encapsulated substance (e.g., a polynucleotide) is fed into at least one material-feeding microchannel on a substrate such as shown in FIG. 1, a fluid (liquid material) containing a substance having a charge opposite to that of the encapsulated substance (e.g., a cationic compound) is fed into at least one other material-feeding microchannel on the substrate, and these fluids are caused to flow from the material-feeding microchannels to the reaction microchannel at a flow rate suitable for maintaining an interface between the fluids in the reaction microchannel (e.g., 0.05 to 100 µL/min, preferably 0.5 to 20 µL/min). The target charged complex can be efficiently obtained on a small scale thereby as a result.

Then the fluid containing the resulting complex can be fed into at least one of the material-feeding microchannels, an envelope-forming fluid (for example, a liquid containing a lipid and other added ingredients) can be fed into at least one of the other material-feeding microchannels, and microcapsules with the desired properties can be produced by the liquid-liquid interface reaction under predetermined conditions.

The method of producing the microcapsules of the present invention when applied to the production of liposomes that can be used as the aforementioned MENDs is described in detail through the following examples. However, the method of producing the microcapsules of the present invention is in no way intended to be limited to these examples.

EXPERIMENTAL EXAMPLE 1

Figure 4:
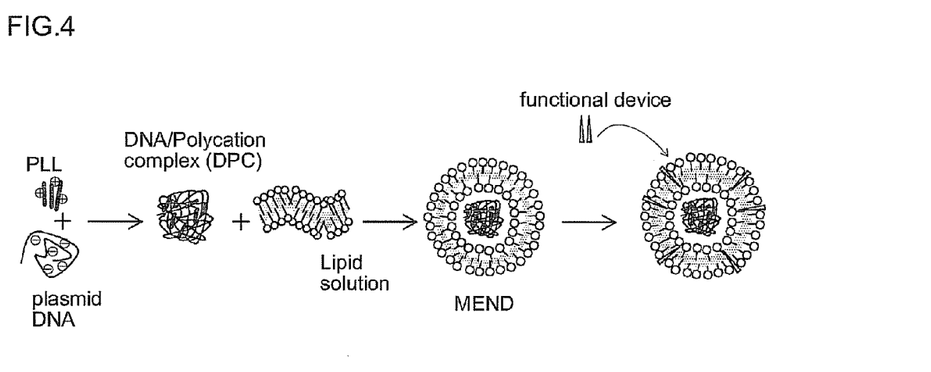
FIG. 4 is an explanatory drawing schematically illustrating the materials used in one example and the reaction product thereof.

As shown in FIG. 4, in the present example commercially available poly-L-lysine (PLL; SIGMA product "O-9882") was used as the cationic polymer (polycation), commercially available plasmid DNA was used as the polynucleotide material, and first a complex of the DNA and polylysine (DNA/Polycation complex; hereinafter DPC) was prepared as a preliminary step.

Then a fluid (liquid) containing the resulting DPC and an envelope-forming fluid were used to produce liposomes. A lipid membrane-forming material (liquid) containing a PEG-modified lipid, etc., was used in the present example.

Figure 5:
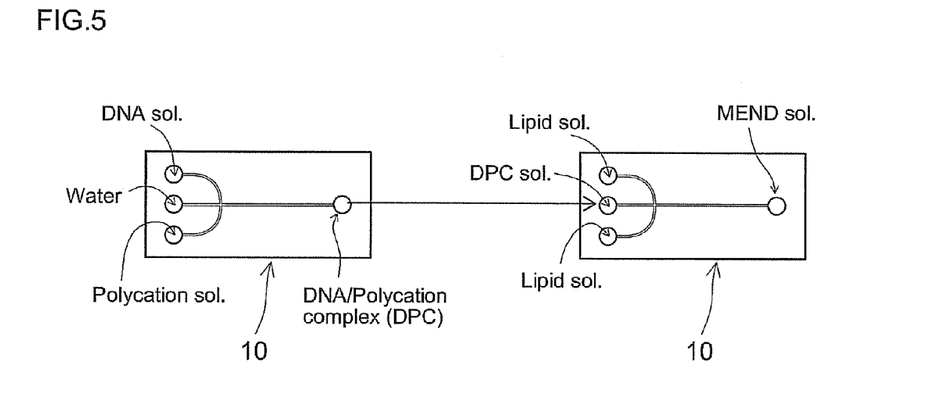
FIG. 5 is an explanatory drawing schematically illustrating the flow of the production process of one example.

More specifically, a quartz glass substrate with the shape shown in FIG. 1 (a 35 mm×75 mm microchip, microchannels 100 µm wide by 30 µm deep) was used to produce the DPC. More specifically, the plasmid DNA (pcDNA3.1(+)luc) and PLL were each dissolved in distilled water, and the concentration was adjusted within the range of 0.01 to 1 mg/mL (in this case, 0.1 mg/mL). Then, as shown in FIG. 5, distilled water was fed into the center channel of the three material-feeding microchannels. Simultaneously, the above plasmid DNA solution was fed into one of the adjacent material-feeding microchannels and the above PLL solution was fed into the other adjacent material-feeding microchannel.

Thus, a non-material-containing fluid (in this case, distilled water) containing neither polynucleotide nor cationic compound was fed into one of the material-feeding microchannels; the fluid containing the polynucleotide (in this case, negatively charged plasmid DNA) was caused to flow on one side of the non-material-containing fluid flowing through an area of one part of the reaction microchannel while maintaining an interface with that non-material-containing fluid; and the fluid containing the cationic compound (in this case, positively charged PLL) was caused to flow on the other side of the non-material-containing fluid flowing through an area of one part of the reaction microchannel to obtain a condensate complex (in this case, DPC) with great efficiency.

In the present example, the flow rate of the fluids flowing through each material-feeding microchannel and the reaction microchannel was set to 10 μL/min on the syringe pumps (AS ONE Corporation).

Figure 6:
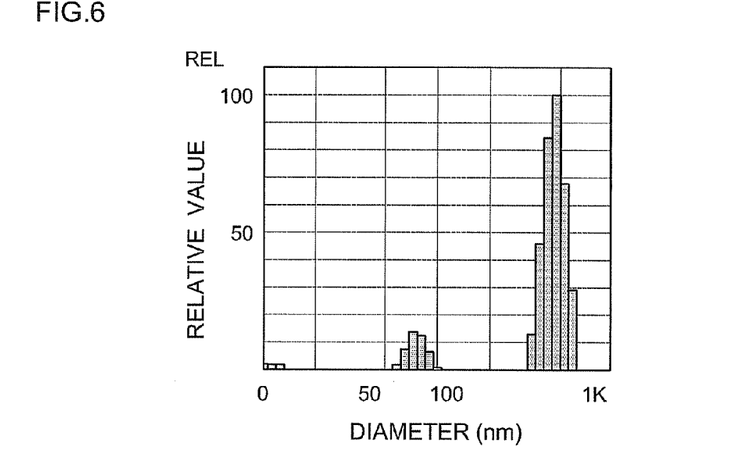
FIG. 6 is a graph showing the particle size distribution of the DNA/polylysine complex (DPC) obtained in one example.

Next the liquid that had flowed through the reaction microchannel was collected. Then using a commercially available light-scattering particle size analyzer/zeta potential analyzer (Particle Sizing Systems Co.), the particle size distribution of the resulting DPC condensate (DNA condensate) was measured. FIG. 6 shows the results (particle size distribution). As can be clearly seen from the graph in FIG. 6, the particle size of the resulting DPC condensate was concentrated in the 50 to 100 nm range, and the range of the particle size distribution was narrow. In addition, the particle distribution peak value (i.e., the mode diameter) was approximately 70 nm (see FIG. 6).

Next, as shown in FIG. 5, using a substrate of the same shape, fluid (liquid) containing the DPC obtained from the above manner was fed into the center channel of the three material-feeding microchannels. Simultaneously, the lipid membrane-forming fluid (solution) was fed into the two adjacent material-feeding microchannels.

Not only in this experimental example, but also in general, the lipid concentration when producing this type of microcapsule (liposome) is not being limited, but about 0.01 to 200 mg/mL is suitable and about 0.1 to 100 mg/mL is preferred. Either an aqueous or organic solvent can be used, but a buffer with a suitable pH (6.5 to 7.5, more preferably 7.0 to 7.5) is preferred. In this experimental example the following ingredients:

(1) 260 μL of a mixed solution of 20 mg/mL DOPE (dioleoyl phosphatidylethanolamine), 0.2 M OGP (n-Octyl-β-D-glucopyranoside) and 5 mM HEPES;
(2) 60 μL of a mixed solution of 40 mg/mL PEG (1,2-distearoyl-sn-glycero-3-phosphoethanolamine-N-[methoxy (polyethylene glycol)-2000]: Avanti™, Polar Lipids Inc., N0. 880120P), 0.2 M OGP, and 5 mM HEPES;
(3) 400 μL of a mixed solution of 1 mg/mL DCP (dicetyl phosphate), 0.4 M OGP, and 10 mM HEPES;
(4) 400 μL of deionized distilled water; and
(5) 400 μL of mixed solution of 0.2 M OGP and 5 mM HEPES were mixed together to prepare the lipid solution (i.e., the envelope-forming fluid used in this experimental example), and the lipid solution was fed into the two material-feeding microchannels as noted above.

In this experimental example, the flow rate of the fluids flowing through each material-feeding microchannel and the reaction microchannel was set to 10 μL/min on the syringe pumps (AS ONE Corporation), and the flow was carried out at room temperature (20 to 35° C., preferably 25 to 30° C.).

Figure 7:
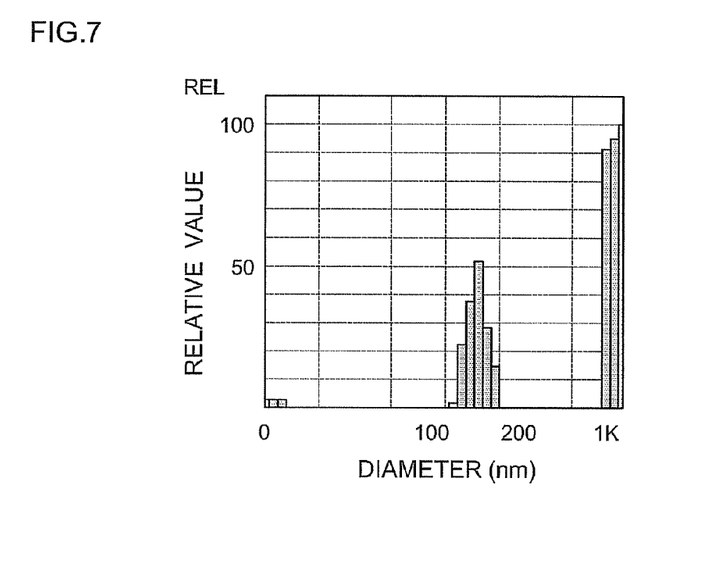
FIG. 7 is a graph showing the particle size distribution of microcapsules (liposomes) obtained in one example.

Next the liquid that had flowed through the reaction microchannel 8 was collected. Then using a commercially available light-scattering particle size analyzer/zeta potential analyzer (Particle Sizing Systems Co.), the particle size distribution of the resulting liposomes (MENDs) was measured. FIG. 7 shows the results (particle size distribution). As can be clearly seen from the graph in FIG. 7, the particle size of the resulting liposomes (MENDs) was concentrated in the 100 to 200 nm range, and the range of the particle size distribution was narrow. In addition, the particle distribution peak value was approximately 150 nm (see FIG. 7).

The above results confirmed that microcapsules can be efficiently produced on a substrate using the method of the present invention.

EXPERIMENTAL EXAMPLE 2

Next, using FITC-labeled polylysine, an FITC-labeled DPC (DNA condensate) solution was prepared according to the above method. Furthermore, a rhodamine-labeled lipid solution was prepared by air drying rhodamine-labeled DOPE in a microtube and redissolving it in the above lipid solution. Then the same microcapsule preparation process as described above was carried out to prepare labeled microcapsules (MENDs). When the resulting MENDs were observed using a laser scanning confocal microscope (Carl Zeiss), it was confirmed that the desired encapsulated substance (in this case FITC-labeled DPC) was located inside the MENDs.

EXPERIMENTAL EXAMPLE 3

Figure 8:
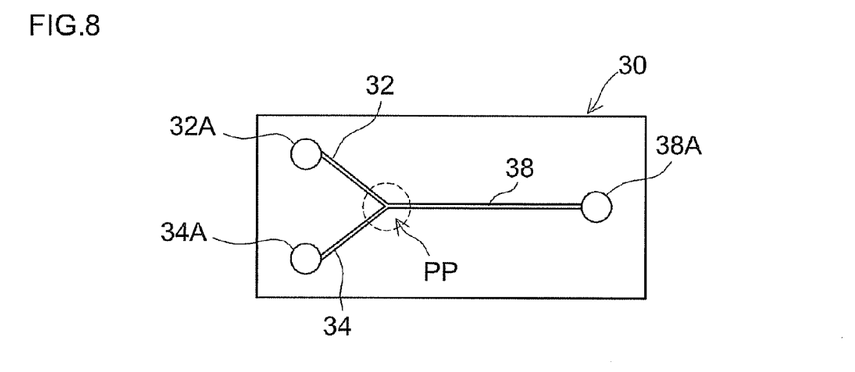
FIG. 8 is an explanatory drawing schematically illustrating one example of a microreactor configuration.

In the present example a DPC was prepared using a quartz glass substrate 30 (a 35 mm×75 mm microreactor, microchannels 100 μm wide by 40 μm deep) having two material-feeding microchannels 32, 34 configured in a Y-shape (two-way) as shown in FIG. 8.

In other words, plasmid DNA (pcDNA3.1(+)luc) and PLL were each dissolved in distilled water to make a 0.1 mg/mL plasmid DNA solution and a total of 8 kinds of PLL solutions with concentrations of 0.005 mg/mL, 0.01 mg/mL, 0.02 mg/mL, 0.03 mg/mL, 0.05 mg/mL, 0.06 mg/mL, 0.08 mg/ml, and 0.1 mg/mL. Then the above plasmid DNA solution was fed into the reservoir (inlet) 32A of one material-feeding microchannel 32 and a PLL solution having one of the above concentrations was fed into the reservoir (inlet) 34A of the other material-feeding microchannel 34. In the present example, the flow rate of the stock solutions flowing through each material-feeding microchannel 32, 34 was set to 10 μL/min on the syringe pumps (AS ONE Corporation). The duration for preparing one DPC (i.e., the duration of feeding the stock solutions) was set at 10 min.

Figure 9:
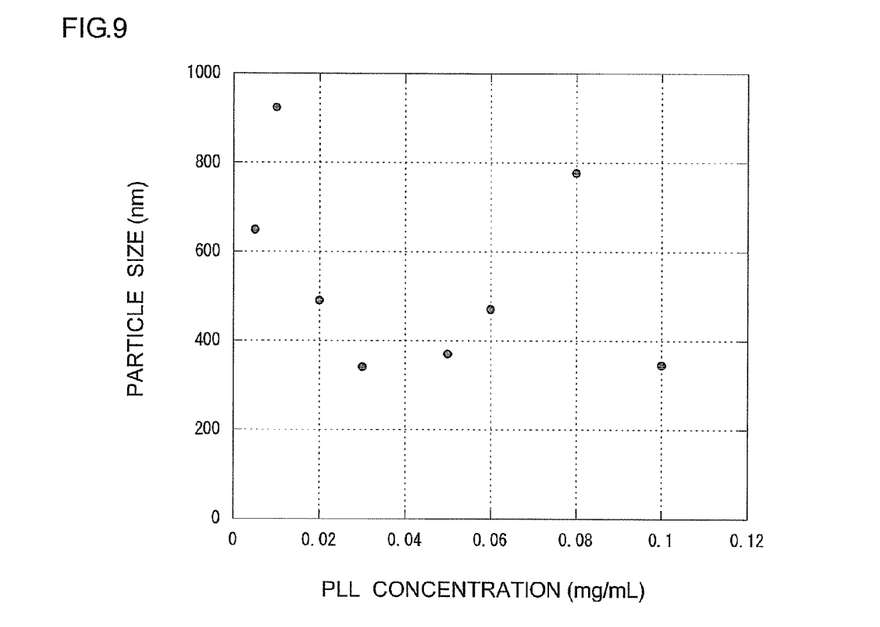
FIG. 9 is a graph showing the relationship between the particle size (peak particle size) of the DNA/polylysine complex (DPC) obtained in one example and the concentration of PLL used.

Ten minutes after feeding of the above stock solutions was started, the liquid that had flowed through the reaction microchannel 38 was collected from the reservoir (outlet) 38A. As in Experimental Example 1, using a commercially available light-scattering particle size analyzer/zeta potential analyzer (Particle Sizing Systems Co.), the particle size distributions and peak particle sizes of the resulting DPC condensates (DNA condensates) were measured. FIG. 9 shows the results (particle size distribution). Each point on the graph represents the mean value of 3 measurement results.

As can be clearly seen from the graph in FIG. 9, DPCs (in this case, DNA/polylysine complexes) with a particle size (peak particle size) generally in the range of 200 nm to 1000 nm were obtained. The particle size of the obtained DPCs changed according to the PLL concentration. Although the detailed data are not presented herein, when the substrate (microreactor) 30 used in this example having the material-feeding microchannels 32 and 34 in a Y-shape (two-way) was observed using a laser scanning confocal microscope (Carl Zeiss), a slight accumulation of DPC at the convergence point PP of each microchannel 32, 34, 38 was observed. This accumulation is believed to have affected the flow (flow rate) of the liquids, and may even be the cause of the variation in particle size (peak value) of the formed DPC.

EXPERIMENTAL EXAMPLE 4

In the present example, a quartz glass substrate as in Experimental Example 1 with three material-feeding microchannels and the shape shown in FIG. 1 (a 35 mm×75 mm microchip, microchannels 100 μm wide by 40 μm deep) was used to produce the DPC.

More specifically, plasmid DNA (pcDNA3.1(+)luc) and PLL were each dissolved in distilled water to make a 0.01 mg/mL plasmid DNA solution and a total of 5 kinds of PLL solutions with concentrations of 0.004 mg/mL, 0.006 mg/mL, 0.008 mg/mL, 0.01 mg/mL, and 0.02 mg/mL.

Then distilled water was fed into the center channel of the three material-feeding microchannels. Simultaneously, the above plasmid DNA solution was fed into an adjacent material-feeding microchannel on one side, and the PLL solution having one of the above concentrations was fed into the adjacent material-feeding microchannel on the other side. In the present example, the flow rate of the stock solutions flowing through each material-feeding microchannel was set to 10 μL/min on the syringe pumps (AS ONE Corporation). The duration for preparing one DPC (i.e., the duration of feeding the stock solutions) was set at 10 min.

Figure 10:
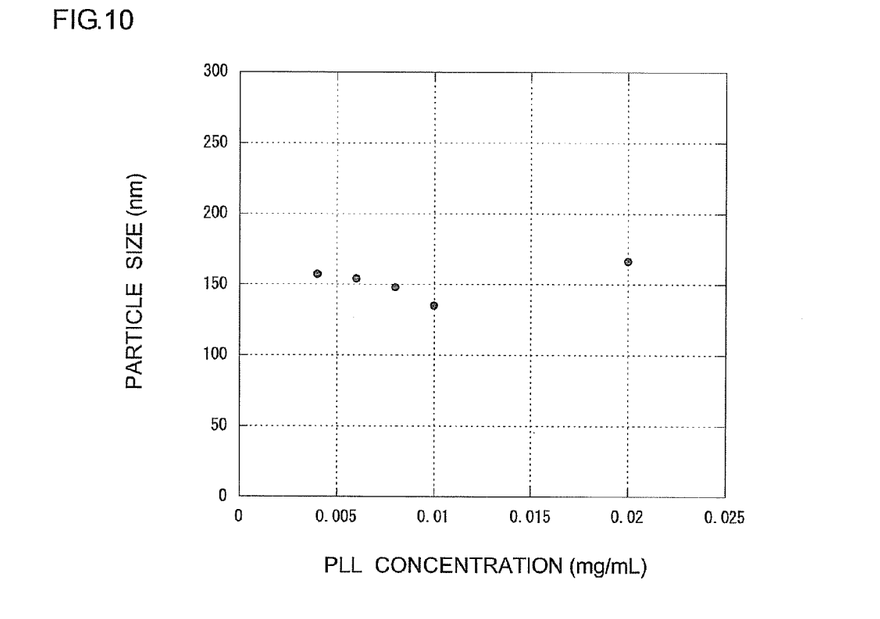
FIG. 10 is a graph showing the relationship between the particle size (peak particle size) of the DNA/polylysine complex (DPC) obtained in another example and the concentration of PLL used.

Ten minutes after feeding of the above stock solutions was started, the liquid that had flowed through the reaction microchannel was collected from the reservoir (outlet). As in Experimental Example 3, using a commercially available light-scattering particle size analyzer/zeta potential analyzer (Particle Sizing Systems Co.), the particle size distributions and peak particle sizes of the resulting DPC condensates (DNA condensates) were measured. FIG. 10 shows the results (particle size distribution). Each point on the graph represents the mean value of 3 measurement results.

As can be clearly seen from the graph in FIG. 10, regardless of the concentration (0.004-0.02 mg/mL) of the PLL used, DPCs (in this case, DNA/polylysine complexes) with a particle size (peak particle size) generally in the range of 100 nm to 200 nm (more specifically, 130 to 170 nm, and especially about 150 nm±10 nm) were stably obtained. Although the detailed data are not presented herein, when the substrate was observed using a laser scanning confocal microscope (Carl Zeiss), no accumulation of DPC at the convergence point (see symbol P in FIG. 1) of the microchannels was being observed. Additionally, the location where the stock solutions mixed together (i.e., the liquid-liquid interface of the fluids that had flowed through the material-feeding microchannels: see symbol B in FIG. 2) had extended from the microchannel convergence point to the vicinity of the reaction microchannel reservoir (outlet). It is believed that these factors contributed to the stability in particle size (peak value) of the DPCs that were formed.

EXPERIMENTAL EXAMPLE 5

In the present example, DPCs were produced using the same substrate (microreactor) and materials as in Experimental Example 4. In the present example, the PLL concentration and the plasmid DNA concentration were each fixed at 0.01 mg/mL, and the rate of feeding the stock solutions into the material-feeding microchannels (flow rate) was set at 1 μL/min, 2.5 μL/min, 5 μL/min, 7.5 pt/min or 10 μL/min to produce the DPCs.

Figure 11:
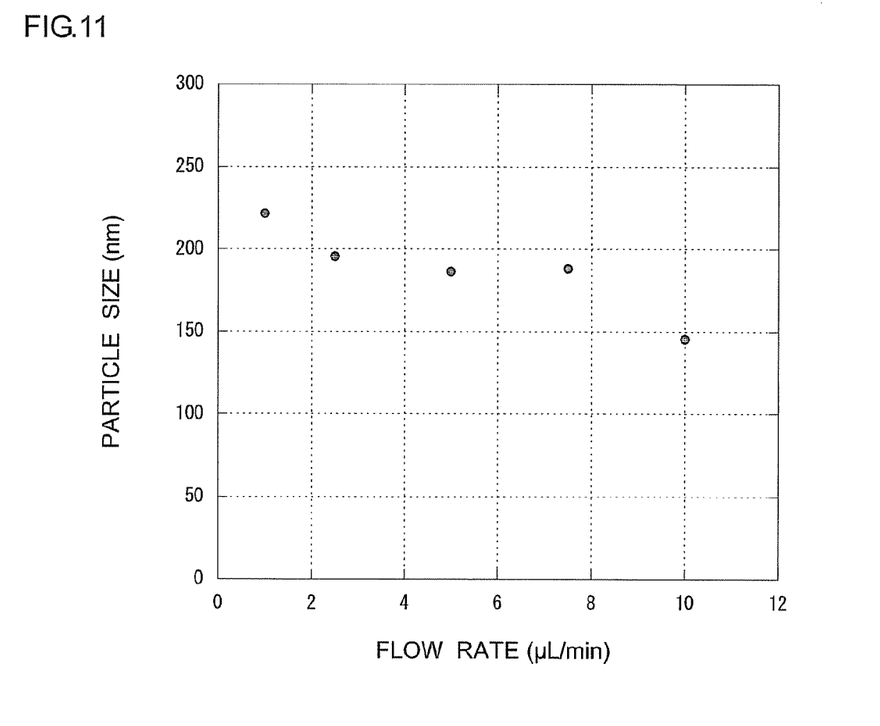
FIG. 11 is a graph showing the relationship between the particle size (peak particle size) of the DNA/polylysine complex (DPC) obtained in another example and the flow rate of a stock solution used.

Ten minutes after feeding of the above stock solutions was started, the liquid that had flowed through the reaction microchannel was collected from the reservoir (outlet). As in Experimental Examples 3 and 4, using a commercially available light-scattering particle size analyzer/zeta potential analyzer (Particle Sizing Systems Co.), the particle size distributions and peak particle sizes of the resulting DPC condensates (DNA condensates) were measured. FIG. 11 shows the results (particle size distribution). Each point on the graph represents the mean value of 3 measurement results.

As can clearly be seen from the graph in FIG. 11, as the flow rate (1 to 10 μL/min) of the stock solutions decreased, the particle size (peak particle size) of the obtained DPCs gradually increased. More specifically, at the same flow rate of 10 μL/min used in Experimental Example 3, DPCs with a particle size (peak particle size in the particle size distribution) of approximately 150 nm were stably obtained. By reducing the flow rate of the stock solutions to about 2.5 to 7.5 μL/min, DPCs with a particle size (peak particle size of the particle size distribution) of approximately 200 nm were stably obtained. Additionally, by reducing the flow rate of the stock solutions to 1 μL/min, DPCs with a particle size (peak particle size of the particle size distribution) exceeding 200 nm (typically, 200 to 250 nm) were stably obtained.

Although detailed data are not presented herein, when the flow rate of the fluids flowing through the material-feeding microchannels and reaction microchannel was varied from 1 to 10 μL/min and the DPCs obtained thereby were used in the step for producing liposomes (MENDs) with the same materials and methods as in Experimental Example 1, it was found that as the flow rate of the stock solutions decreased, the particle size (peak particle size) of the resulting liposomes (MENDs) gradually increased.

As can be clearly seen from the above findings, in the method of the present invention the particle size (particle distribution) of the resulting MENDs and DPCs can be controlled by adjusting the flow rate of the solutions (liquids) that flow through the microchannels on the substrate. More specifically, using a type of substrate in the shape of a trident that connects three material-feeding microchannels and one reaction microchannel (preferably a substrate as illustrated in FIGS. 1 and 2 wherein the each of the material-feeding microchannels 12, 13, 14 intersects orthogonally with its adjacent channel) thereby enabling a smooth flow of the solution downstream from the above junction point P is preferred.

The liposomes (MENDs) obtained in the above manner can be suitably used as a vector (typically, a gene vector) to deliver a desired substance (encapsulated substance) into a cell. Such microcapsules (liposomes) can be used in the form of a liquid dispersion. A buffer such as physiological saline, phosphate buffer, citrate buffer, acetate buffer and the like can be used as the dispersion medium. Various additives such as a saccharide, polyhydric alcohol, water-soluble polymer, non-ionic surfactant, antioxidant, pH regulator, hydrating agent, and the like can be added to the liquid dispersion and used therein. Moreover, such microcapsules (liposomes) can be used either in vivo or in vitro. Examples of the route of administration when the microcapsules are used in vivo include intravenous, intraperitoneal, subcutaneous, transnasal, and other parenteral routes of administration.

When the microcapsules are used as a gene vector, etc., the introduction of a cell membrane-binding substance to the surface of the envelope (in this case, lipid membrane) is preferred (FIG. 5). The endocytosis rate of the microcapsules as a vector can be increased thereby.

A cell membrane-binding substance is a substance that can bind with a receptor or antigen present on the surface of the cell membrane, and more specific examples include transferrin, insulin, folic acid, hyaluronic acid, an antibody or fragment thereof, sugar chain, growth factor, apolipoprotein, and the like.

Examples of a growth factor include epidermal growth factor (EGF), insulin-like growth factor (IGF), fibroblast growth factor (FGF) and the like. Examples of an apolipoprotein include apo A-1, apo B-48, apo B-100, apo E, and the like. Examples of an antibody fragment include an Fab fragment, F(ab)'2 fragment, single chain antibody fragment (scFv) and the like.

The cell membrane-binding substance can be introduced onto the liposome surface by the joining thereof to a hydrophilic polymer on the surface of the liposome. For example, by reacting the functional group of a hydrophilic polymer (including a functional group artificially introduced into the hydrophilic polymer) with a functional group of the cell membrane-binding substance (including a functional group artificially introduced into the cell membrane-binding substance), the cell membrane-binding substance can be joined to the hydrophilic polymer by a covalent bond. Combinations of functional groups that can form covalent bonds include the following: amino group/carboxyl group; amino group/halogenated acyl group; amino group/N-hydroxy succinimide ester group; amino group/benzotriazole carbonate group; amino group/aldehyde group; thiol group/maleimide group; thiol group/vinyl sulfone group; and the like.

Thus, microcapsules such as MENDs and the like can be produced efficiently on an extremely small substrate (microchip) in accordance with the present invention. For example, 30 hours or more would generally be needed to produce the MEND disclosed in patent document 1 above using the conventional method, but with the method disclosed herein, MENDs can be produced in about 20 minutes (depending on the channel length and flow rate), including the above step of producing the complex, by using a substrate (microchip) with the microchannels described above. Furthermore, microchannels with a variety of patterns other than those illustrated in FIGS. 1 and 2 can be formed. Additionally, it is easy to prevent contamination by conducting the interface reaction to produce the microcapsules entirely on the substrate, which is advantageous when producing biological material such as a gene vector.

INDUSTRIAL APPLICABILITY

The method of the present invention is not limited to the above experimental examples, and it can be suitably applied to the manufacture of microcapsules having a low molecular weight substance, e.g., a polynucleotide other than plasmid DNA (such as antisense oligo-DNA, RNA, etc.), protein (enzyme, etc.), or a functional peptide, oligosaccharide, and the like as the encapsulated substance. Additionally, the substrate used in the present method can be mass produced in the same manner as microchips used in conventional methods.

The invention claimed is:
1. A method comprising:
preparing a substrate including a plurality of material-feeding microchannels with a width of 1000 μm or less and a reaction micro channel with a width of 1000 μm or less connected to the plurality of material-feeding microchannels;
feeding a first fluid containing a substance into a first one of the plurality of material-feeding microchannels;
feeding a second fluid containing an envelope-forming material into a second one of the plurality of material-feeding microchannels;
feeding third fluid containing neither the substance nor the envelope-forming material into a third one of the plurality of microchannels;
converging the first fluid, the second fluid and the third fluid from each of the first, the second and the third material-feeding microchannel to the reaction microchannel,
wherein the third fluid flows in the center of the reaction microchannel and separates the first fluid and the second fluid continuously along the length of the reaction microchannel;
forming a microcapsule having a diameter of 1 μm or less by encapsulating the substance within the envelope-forming material in the third fluid; and
collecting the fluid containing the microcapsule flowing through the reaction microchannel.
2. The method according to claim 1, wherein the width of each of the plurality of material-feeding microchannels and the reaction microchannel ranges from 10 μm to 500 μm.
3. The method according to claim 1, wherein
the substrate comprises at least three material-feeding micro channels being connected to the reaction micro channel at one point, and
the second fluid is fed into at least two of the material-feeding micro channels and the first fluid is fed into at least another of the material-feeding microchannels such that the second fluid flows on both sides of the first fluid flowing through a part of an area of the reaction micro channel, while maintaining an interface with the first fluid.
4. The method according to claim 3, wherein at least a part of the substance is a polynucleotide, and the envelope is a membrane comprising a lipid.
5. The method according to claim 4, wherein
a complex of a polynucleotide and a cationic compound is used as the substance, and
the method further comprises a step of producing the complex comprising:
preparing a second substrate including a second plurality of material-feeding microchannels with a width of 1000 μm or less and a second reaction micro channel with a width of 1000 μm or less connected to the plurality of material-feeding microchannels;
feeding a fluid containing the polynucleotide into at least one of the second plurality of material-feeding microchannels;
feeding a fluid containing the cationic compound into at least another one of the second plurality of material-feeding microchannels;
converging the fluid containing the polynucleotide and the fluid containing the cationic compound from each material-feeding microchannel to the reaction microchannel so as to continuously maintain a fluid-fluid interface of the fluids along the reaction microchannel;
causing a formation of the complex of the polynucleotide and the cationic compound in the reaction microchannel; and
collecting the fluid containing the complex flowing through the reaction microchannel.

6. The method according to claim 5, wherein
the substrate comprises at least three material-feeding micro channels connected to the reaction micro channel at one point,
a non-material-containing fluid containing neither the polynucleotide nor the cationic compound is fed into at least one of the material-feeding micro channels, the fluid containing the polynucleotide is fed into at least one of the material-feeding micro channels and the fluid containing the cationic compound is fed into at least another one of the material-feeding micro channels such that the fluid containing the polynucleotide flows on one side of the non-material-containing fluid flowing through a part of an area of the reaction microchannel while maintaining an interface with the nonmaterial-containing fluid, and such that the fluid containing the cationic compound flows on the other side of the non-material-containing fluid while maintaining an interface therewith.

7. A substrate for producing a microcapsule comprising:
at least three material-feeding microchannels with a width of 1000 μm or less; and
a reaction micro channel with a width of 1000 μm or less,
wherein all of the material-feeding microchannels are connected to the reaction microchannel at one point,
wherein the microcapsule produced utilizing the substrate has a diameter of 1 μm or less and comprises an envelope encapsulating a material.

8. The substrate according to claim 7, wherein the width of each of the at least three material-feeding microchannels and the reaction micro channel ranges from 10 μm to 500 μm.

9. The method according to claim 1, wherein
the fluid containing the encapsulated substance is a solution containing the encapsulated substance or a dispersion containing the encapsulated substance, and
the envelope-forming fluid is a solution containing the envelope-forming material or a dispersion containing the envelope-forming material.

10. The method according to claim 5, wherein
the fluid containing the polynucleotide is a solution containing the polynucleotide or a dispersion containing the polynucleotide, and
the fluid containing the cationic compound is a solution containing the cationic compound or a dispersion containing the cationic compound.

* * * * *